(12) United States Patent
Ellson et al.

(10) Patent No.: US 9,939,352 B2
(45) Date of Patent: Apr. 10, 2018

(54) METHOD AND SYSTEM FOR DETERMINING THE CONCENTRATION OF AN ANALYTE IN A FLUID SAMPLE

(71) Applicant: Labcyte Inc., Sunnyvale, CA (US)

(72) Inventors: Richard N. Ellson, Palo Alto, CA (US); Richard G. Stearns, Felton, CA (US); Joseph D. Olechno, Hayward, CA (US); Ian Sinclair, Warrington (GB); Jonathan Wingfield, Macclesfield (GB)

(73) Assignee: LABCYTE, INC., San Jose, CA (US)

( * ) Notice: Subject to any disclaimer, the term of this patent is extended or adjusted under 35 U.S.C. 154(b) by 252 days.

(21) Appl. No.: 14/887,320

(22) Filed: Oct. 19, 2015

(65) Prior Publication Data

US 2016/0109336 A1    Apr. 21, 2016

Related U.S. Application Data

(60) Provisional application No. 62/065,600, filed on Oct. 17, 2014.

(51) Int. Cl.
| | | |
|---|---|---|
| *G01N 1/28* | (2006.01) | |
| *H01J 49/04* | (2006.01) | |
| *C12Q 1/68* | (2018.01) | |
| *G01N 33/68* | (2006.01) | |

(52) U.S. Cl.
CPC ............... *G01N 1/28* (2013.01); *H01J 49/04* (2013.01); *H01J 49/0431* (2013.01); *C12Q 1/68* (2013.01); *G01N 33/6848* (2013.01); *G01N 33/6851* (2013.01); *H01J 49/0422* (2013.01); *Y10T 436/24* (2015.01); *Y10T 436/25875* (2015.01)

(58) Field of Classification Search
CPC ...... G01N 1/28; G01N 33/68; G01N 33/6848; G01N 33/6851; H01J 49/04; H01J 49/0431; H01J 49/0422; C12Q 1/68; Y10T 436/143333; Y10T 436/147777; Y10T 436/17; Y10T 436/173845; Y10T 436/174614; Y10T 436/175383; Y10T 436/204998; Y10T 436/24; Y10T 436/25875
USPC ..... 436/86, 94, 98, 106, 111, 112, 113, 133, 436/173, 181; 435/6.1; 422/68.1
See application file for complete search history.

(56) References Cited

U.S. PATENT DOCUMENTS

| | | |
|---|---|---|
| 2,280,828 A | 4/1942 | Inhoffen |
| 2002/0109084 A1 | 8/2002 | Ellson et al. |
| 2006/0024660 A1* | 2/2006 | Jouin ................. G01N 33/6848 435/4 |
| 2010/0024527 A1 | 2/2010 | LaMarr et al. |
| 2011/0005930 A1 | 1/2011 | Weber et al. |

OTHER PUBLICATIONS

International Search Report of PCT Application No. PCT/US2015/056288 dated Jan. 29, 2016.
Annesley, "Ion Suppression in Mass Spectrometry", Clinical Chemistry, 2003, vol. 49, No. 7, pp. 1041-1044.
Bonfiglio, et al., "The Effects of Sample Preparation Methods on the Variability of the Electrospray Ionization Response for Model Drug Compounds", Rapid Communications in Mass Spectrometry, 1999, vol. 13, pp. 1175-1185.
Keller, et al., "Interferences and contaminants encountered in modern mass spectrometry", Analytica Chimica Acta, 2008, pp. 1-11.
Sterner, et al., "Signal suppression in electrospray ionization Fourier transform mass spectrometry of multi-component samples", Journal of Mass Spectrometry, 2000, vol. 35, pp. 385-391.
Weaver, et al., "Identification and reduction of ion suppression effects on pharmacokinetic parameters by polyethylene glycol 400", Rapid Communications in Mass Spectrometry, 2006, vol. 20, pp. 2559-2564.

* cited by examiner

*Primary Examiner* — Maureen Wallenhorst
(74) *Attorney, Agent, or Firm* — Dianne E. Reed; VLP Law Group, LLP

(57) ABSTRACT

A method and system are provided for detecting the concentration of an analyte in a fluid sample. The method and system involve analysis of a volatilized, ionized fluid sample using a mass spectrometer or other ionic analyte detection device that provides a signal proportional in intensity to the quantity of ionized analyte detected. The improvement involves replacement of a necessary non-analyte component in the fluid sample with a substitute component that serves the same purpose as the original component but is either more volatile than the original component and/or the analyte or undergoes a reaction to provide lower molecular weight reaction products, and results in an increased intensity in signal and signal-to-noise ratio. Acoustic fluid ejection is a preferred method of generating nanoliter-sized droplets of fluid sample that are then volatilized, ionized, and analyzed. Also provided are zwitterionic compounds suitable as the substitute components that when ionized and heated decompose to provide carbonic dioxide, a nitrogenous species such as ammonia, an amine, or nitrogen gas, and a volatile aromatic compound.

39 Claims, 5 Drawing Sheets p-TsOH
Toluene alkaline
hydrolysis

Compound (30)

METHOD AND SYSTEM FOR DETERMINING THE CONCENTRATION OF AN ANALYTE IN A FLUID SAMPLE

CROSS-REFERENCE TO RELATED APPLICATION

This application claims priority under 35 U.S.C. § 119(e)(1) to provisional U.S. Patent Application Ser. No. 62/065,600, filed Oct. 17, 2014, the disclosure of which is incorporated by reference herein.

TECHNICAL FIELD

The present invention relates generally to improved methods for detecting the presence or quantity of an analyte in a fluid sample, and more particularly relates to improvements in such methods where nanoliter-sized fluid droplets are generated and the sample accurately analyzed. The invention finds utility in the fields of analytical chemistry, biological research, pharmaceuticals, and medicine.

BACKGROUND

Accurate determination of the presence, identity, concentration, and/or quantity of an ionized species in a sample is critically important in many fields. Most techniques used in such analyses involve ionization of species in a fluid sample prior to introduction into the analytical equipment employed. The choice of ionization method will depend on the nature of the sample and the analytical technique used, and many ionization methods are available, including, without limitation, chemical ionization, electron impact ionization, desorption chemical ionization, and atmospheric pressure ionization, including electrospray ionization and atmospheric pressure chemical ionization.

The presence of contaminants in biological samples undergoing analysis is obviously problematic for a number of reasons. Contaminants might cause interference with the analytical procedure, chemically or physically altering the sample or the analyte itself. Contaminants may also be mistaken for analyte or vice versa, such that the concentration measured concentration of analyte may be significantly higher or lower than the actual concentration. The same problem can be caused by necessary components of the fluid sample, such as buffer salts, surfactants, and other species that may be essential for biochemical steps preceding the analysis.

Mass spectrometry is a well-established technique that involves the detection of an analyte in ionized form. In this technique, sample molecules are ionized and the resulting ions are sorted by mass-to-charge ratio. For analytes contained in a fluid sample, the sample is typically converted to an aerosol that undergoes desolvation, vaporization, and ionization in order to form fluid ions.

The presence of non-analyte species can be particularly problematic in mass spectrometry, where analyte concentration may be very low and the number and concentration of contaminants and interfering components may be relatively high. One study has documented over 650 contaminants and interfering components frequently found in biological samples undergoing mass spectrometric analysis. B. O. Keller et al. (2008), "Interferences and contaminants encountered in modern mass spectrometry," Anal. Chim. Acta 627(1):71-81. These include salts, buffering agents, endogenous compounds, surfactants, drugs, metabolites, and proteins. When these species reduce detection sensitivity by decreasing the signal-to-noise ratio and give rise to a flawed analysis, the problem has been characterized as "ion suppression." See Weaver et al. (2006) *Rapid Communications in Mass Spectrometry* 20:2559-64.

It has been postulated that "the main cause of ion suppression is a change in the spray droplet solution properties caused by the presence of nonvolatile or less volatile solutes," i.e., solutes that are nonvolatile or less volatile than the analyte; see Annesley (2003) "Ion Suppression in Mass Spectrometry," in *Clinical Chemistry* 49(7):1041-1044, citing King et al. (2000) *J. Am. Soc. Mass Spectrom.* 11:942-50. The reference explains that the nonvolatile or less volatile contaminants and components change the efficiency of droplet formation or droplet volatilization, which in turn affects the quantity of charged analyte in the gas phase that ultimately reaches the detector. Annesley cites studies showing that molecules of higher mass tend to suppress the signal of smaller molecules and that more polar analytes are susceptible to ion suppression. Annesley at 1042, citing Sterner et al. (2000) *J. Mass Spectrom.* 35:385-91 and Bonfiglio et al. (1999) *Rapid Commun. Mass Spectrom.* 13:1175-85. Weaver et al. cites several possible mechanisms underlying ion suppression: (1) competition for charge between analyte and ion-suppressing agent, leading to reduced ionization of analyte; (2) large concentrations of ion-suppressing agents causing an increase in surface tension as well as an increase in droplet viscosity, in turn resulting in decreased evaporation efficiency; and (3) gas phase reactions between the ionized analyte and other species in the sample, resulting in an overall loss of charge from the analyte ions. Weaver et al. at 2562.

As electrospray ionization (ESI) has a relatively complex ionization mechanism, relying heavily on droplet charge excess, there are additional factors to consider when exploring the cause of ion suppression and potential solutions. It has been widely observed that for many analytes, at high concentrations, ESI exhibits a loss of detector response linearity, perhaps due to reduced charge excess caused by analyte saturation at the droplet surface, inhibiting subsequent ejection of gas phase ions from further inside the droplet. Thus, competition for space and/or charge may be considered as a source of ion suppression in ESI. Both physical and chemical properties of analytes (e.g. basicity and surface activity) determine their inherent ionization efficiency. Biological sample matrices naturally tend to contain many endogenous species with high basicity and surface activity, and the total concentration of these species in the sample will thus quickly reach levels at which ion suppression can be expected.

Another explanation of ion suppression in ESI considers the physical properties of the droplet itself rather than the species present. As noted above, high concentrations of interfering components give rise to increased surface tension and viscosity that in turn reduce evaporation efficiency, and this is known to have a marked effect on ionization efficiency.

An additional theory to explain ion suppression in ESI relates to the presence of non-volatile species that can either cause co-precipitation of analyte in the droplet (thus preventing ionization) or prevent the contraction of droplet size to the critical radius required for ion evaporation and/or charge residue mechanisms to form gas phase ions efficiently. It should also be pointed out that the degree of ion suppression may be dependent on the concentration of the analyte being monitored, and with the ever-increasing demand to lower detection threshold, ion suppression may become a more and more serious problem.

Ion suppression has primarily been addressed by desalting the fluid sample using dialysis, liquid chromatography, solid-phase extraction, or ion exchange. These processes require time, materials, and equipment, and can reduce the available quantity of an already small sample. In addition, certain ionic or ionizable species may be essential to maintain in the sample, such as buffer systems.

An ideal method to address ion suppression would:

Eliminate the need for additional process steps and materials, including clean-up and de-salting;

Eliminate the need for additional processing time;

Be adaptable to use with very small sample sizes, consume a small portion of the small sample size, allow for detection of low analyte concentrations, and be composed of very small droplets; and Be capable of implementation in a high speed analytical system such as high throughput mass spectrometry, optimally enabling analysis of up to at least 50,000 samples per day or more; and Eliminate the need for pre-analysis "clean-up" of the sample to remove contaminants and interfering components.

SUMMARY OF THE INVENTION

Accordingly, the present invention addresses the aforementioned need in the art by providing an improved method for accurately determining the concentration of an analyte in a fluid sample.

In one embodiment, an improved method is provided for determining the concentration of an analyte in a fluid sample that also contains a necessary non-analyte component, where the method comprises volatilizing and ionizing the fluid sample, and introducing the ionized, volatilized sample into an ionic analyte detection device that provides an analyte signal proportional in intensity to the quantity of analyte detected, e.g., a mass spectrometer, wherein the improvement comprises replacing the necessary non-analyte original component with a substitute component that (a) functions as the necessary non-analyte component in the fluid sample, i.e., serves the same purpose with respect to the fluid sample, (b) is more volatile than the original component and/or the analyte, and/or undergoes a chemical reaction to yield at least one reaction product that is more volatile than the original component and/or the analyte, and (c) results in an increase in the intensity of the analyte signal and/or a greater signal to noise ratio than either the signal intensity or signal to noise ratio obtained using the original component.

In another embodiment, acoustic ejection is used to generate nanoliter-sized droplets that are then volatilized, ionized, and analyzed, wherein "nanoliter-sized" droplets are defined herein as droplets of 5 nl or less. In acoustic ejection, an acoustic ejector directs focused acoustic energy into a reservoir containing the fluid sample in a manner that results in the ejection of fluid droplets from the surface of the fluid sample. Acoustic ejection provides many advantages over other droplet generation methodologies; for instance, acoustic fluid ejection devices are not subject to clogging, misdirected fluid or improperly sized droplets, and acoustic technology does not require the use of tubing or any invasive mechanical action. Acoustic ejection technology as described, for example, in U.S. Pat. No. 6,802,593 to Ellson et al., enables rapid sample processing and generation of droplets in the nanoliter or even picoliter range. In addition, acoustic ejection enables control over droplet size as well as repeated generation of consistently sized droplets. See U.S. Pat. No. 6,416,164 B1 to Stearns et al., incorporated by reference herein. As explained in that patent, the size of acoustically ejected droplets from a fluid surface can be carefully controlled by varying the acoustic power, the acoustic frequency, the toneburst duration, and/or the F-number of the focusing lens.

In a further embodiment, a zwitterionic compound is used as the substitute non-analyte component in the method of the invention. Upon volatilization, the zwitterionic compound undergoes a chemical reaction to yield at least one reaction product that is more volatile than the original non-analyte component and/or the analyte.

In another embodiment, a method is provided an improved method is provided for determining the concentration of an analyte in a fluid sample that also contains a necessary non-analyte component, where the method comprises volatilizing and ionizing the fluid sample, and introducing the ionized, volatilized sample into an ionic analyte detection device that provides an analyte signal proportional in intensity to the quantity of analyte detected, where a substitute component is selected to replace the necessary non-analyte component and, upon volatilizing the fluid sample, undergoes a reaction to yield at least one reaction product that is more volatile than the necessary original component and/or the analyte.

In another embodiment, a method is provided as above wherein the aforementioned reaction is a decomposition reaction.

In a further embodiment, a method is provided as above wherein the reaction involves chemical, photolytic, or thermal cleavage of a linkage in the substitute component that provides lower molecular weight reaction products that do not cause any significant ion suppression and/or are more volatile than the original component.

In still a further embodiment, a system is provided for determining the concentration of an analyte in a fluid sample that comprises a mass spectrometer, an acoustic ejector to generate droplets of fluid sample, and a means for volatilizing and ionizing the droplets prior to introduction into the mass spectrometer, the improvement which comprises replacing at least one necessary component in the fluid sample with a substitute component that serves the same function as the original component but results in an increase in intensity of analyte signal and/or an increase in signal-to-noise ratio relative to the intensity of the analyte signal and/or signal-to-noise ratio, respectively, obtained using the original component.

In another embodiment, the substitute component of the system contains a linkage that can be chemically, thermally, or photolytically cleaved to provide lower molecular weight reaction products that do not cause any significant ion suppression and/or are more volatile than the original component. When the substitute component contains a photolytically cleavable linkage, the system further includes a source of radiation effective to cleave the linkage.

The method and system of the invention generally provide for an increase in the intensity of analyte signal and/or a greater signal-to-noise ratio that is at least 10% and preferably at least 25% relative to the intensity of the analyte signal and the signal-to-noise ratio obtained without the substitute component.

DETAILED DESCRIPTION OF THE INVENTION

Figure 1:
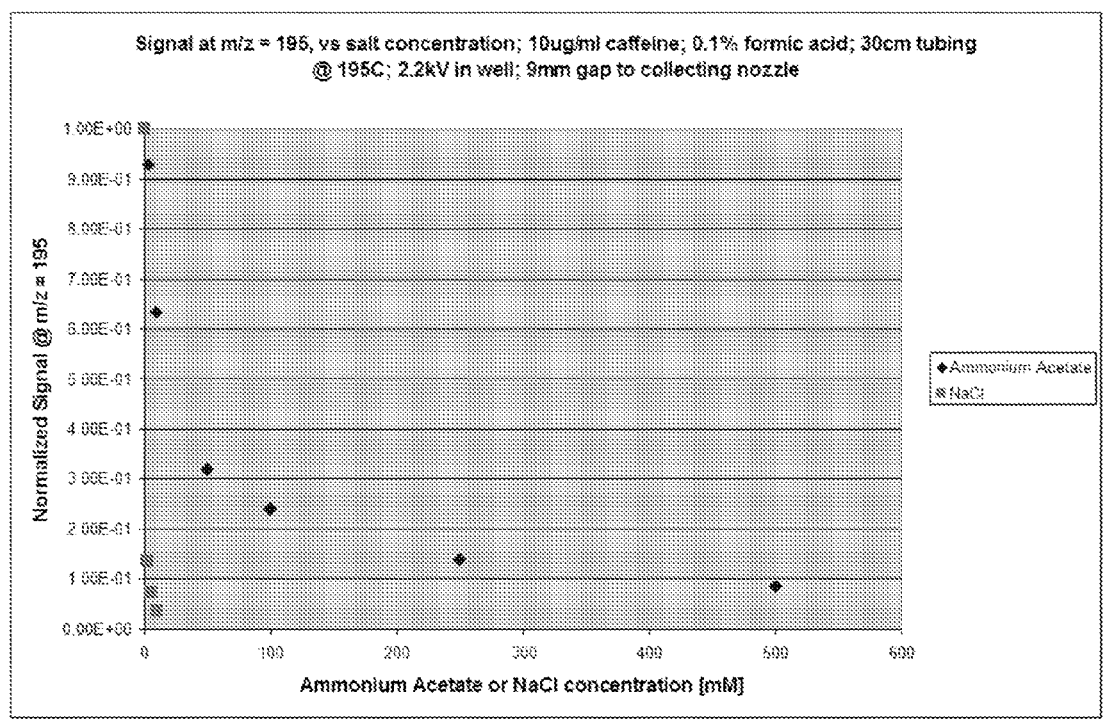
FIG. 1 is a plot of normalized signal at m/z=195 versus ammonium acetate (♦) or sodium chloride (■) concentration (mM), as described in connection with the mass spectrometric detection of caffeine described in Example 1.

Unless defined otherwise, all technical and scientific terms used herein have the meaning commonly understood by one of ordinary skill in the art to which the invention pertains. Specific terminology of particular importance to the description of the present invention is defined below.

In this specification and the appended claims, the singular forms "a," "an" and "the" include plural referents unless the context clearly dictates otherwise. Thus, for example, "an analyte" refers not only to a single analyte but also to a combination of two or more different analytes, "a substitute component" refers to a single such component or to a plurality (e.g., a mixture) of components, and the like.

The term "ionizable" as used herein refers to a species that is capable of undergoing ionization. As such, an "ionizable" species herein may be in electronically neutral form or in ionized (or "ionic") form, as an individual ion or as a component of a salt. The ionizable species may also be present in both electrically neutral and ionized forms, such as will be the case in a buffer system. As an example, acetic acid ($CH_3COOH$) is an ionizable compound that may be present in electronically neutral form, with a protonated carboxyl group, or it may be present in ionized form, with the proton removed to give the acetate ion ($CH_3COO^-$), or it may be present as a combination of the electronically neutral and ionized forms. As another example, a zwitterion containing a carboxylic acid group and an amino group may be in electrically neutral form or in ionized form in which the carboxylic acid group is ionized to carboxylate and the amino group is protonated to give a cationic nitrogen-containing substituent.

The term "volatile" is used herein to refer to the relative tendency of an ion, salt, or compound to leave the surface of a fluid droplet and enter the vapor phase under the vaporization conditions and using the vaporization methods discussed herein. The term is used in a comparative sense herein, such that the substitute species is "volatile" insofar as it is more likely than either the original non-analyte component or the analyte to volatilize under the volatilization conditions employed in conjunction with described method.

The terms "contaminant" and "component" are used to refer to species in the fluid sample that cause ion suppression. The term "contaminant," however, refers to a species that is unintentionally or accidentally introduced into the sample and may have been present in a solvent, reagent, surfactant, or the like, while the term "component" refers to a species that serves a necessary and intended purpose, such as species that are required for biochemical processing preceding the analysis and/or species that are necessary to maintain a chemical or physical parameter of the fluid sample, e.g., buffer systems to maintain pH.

The terms "acoustic radiation" and "acoustic energy" are used interchangeably herein and refer to the emission and propagation of energy in the form of sound waves. As with other waveforms, acoustic radiation may be focused using a focusing means, as discussed below.

The terms "focusing means" and "acoustic focusing means" refer to a means for causing acoustic waves to converge at a focal point, either by a device separate from the acoustic energy source that acts like a lens, or by the spatial arrangement of acoustic energy sources to effect convergence of acoustic energy at a focal point by constructive and destructive interference. A focusing means may be as simple as a solid member having a curved surface, or it may include complex structures such as those found in Fresnel lenses, which employ diffraction in order to direct acoustic radiation. Suitable focusing means also include phased array methods as are known in the art and described, for example, in U.S. Pat. No. 5,798,779 to Nakayasu et al. and Amemiya et al. (1997) *Proceedings of the 1997 IS&T NIP13 International Conference on Digital Printing Technologies*, pp. 698-702.

The terms "acoustic coupling" and "acoustically coupled" used herein refer to a state wherein an object is placed in direct or indirect contact with another object so as to allow acoustic radiation to be transferred between the objects without substantial loss of acoustic energy. When two items are indirectly acoustically coupled, an "acoustic coupling medium" is needed to provide an intermediary through which acoustic radiation may be transmitted. Thus, an ejector may be acoustically coupled to a fluid, e.g., by immersing the ejector in the fluid or by interposing an acoustic coupling medium between the ejector and the fluid to transfer acoustic radiation generated by the ejector through the acoustic coupling medium and into the fluid.

The term "reservoir" as used herein refers to a receptacle or chamber for holding or containing a fluid. Thus, a fluid in a reservoir necessarily has a free surface, i.e., a surface that allows a droplet to be ejected therefrom. In its one of its simplest forms, a reservoir consists of a solid surface having sufficient wetting properties to hold a fluid merely due to contact between the fluid and the surface.

The term "fluid" as used herein refers to matter that is nonsolid or at least partially gaseous and/or liquid. A fluid may contain a solid that is minimally, partially or fully solvated, dispersed or suspended. Examples of fluids include, without limitation, aqueous liquids (including water per se and salt water) and nonaqueous liquids such as organic solvents and the like.

The invention accordingly provides an improved method for determining the concentration of an analyte in a fluid sample, where the fluid sample contains, in addition to the analyte, a necessary non-analyte component, for instance a buffer system including a buffer salt for maintaining pH or a salt for maintaining ionic strength, and wherein the method involves volatilizing and ionizing the fluid sample and introducing the ionized, volatilized sample into an ionic analyte detection device, such as a mass spectrometer, that generates an analyte signal proportional in intensity to the quantity of ionized analyte detected. The improvement provided by the invention involves employing a substitute component for the original non-analyte component that will serve the same purpose as the original component but is more volatile than the original component and/or the analyte or undergoes a chemical reaction upon volatilization to yield a reaction product that is more volatile than the original component and/or the analyte. The substitute component results in a stronger analyte signal and/or an increased signal-to-noise ratio relative to the analyte signal and signal-to-noise ratio obtained with the original non-analyte component. Preferred substitute components, at least in part because of volatility considerations, increase the signal-to-noise ratio by at least 20%, and particularly preferred such components increase the signal-to-noise ratio by 50% or more. The purpose of the necessary non-analyte component may be, as noted, maintaining a pre-determined pH or a required ionic strength.

The analyte in the fluid sample may be any analyte of interest. Examples of analytes include, without limitation, drugs, metabolites, inhibitors, ligands, receptors, catalysts, synthetic polymers, and allosteric effectors. Often, the analyte is a "biomolecule," i.e., any organic molecule, whether naturally occurring, recombinantly produced, chemically synthesized in whole or in part, or chemically or biologically modified, that is, was or can be a part of a living organism. The term encompasses, for example, nucleotidic analytes, peptidic analytes, and saccharidic analytes.

Nucleotidic analytes may be nucleosides or nucleotides per se, but may also comprise nucleosides and nucleotides containing not only the conventional purine and pyrimidine bases, i.e., adenine (A), thymine (T), cytosine (C), guanine (G) and uracil (U), but also protected forms thereof, e.g., wherein the base is protected with a protecting group such as acetyl, difluoroacetyl, trifluoroacetyl, isobutyryl or benzoyl, and purine and pyrimidine analogs. Suitable analogs will be known to those skilled in the art and are described in the pertinent texts and literature. Common analogs include, but are not limited to, 1-methyladenine, 2-methyladenine, $N^6$-methyladenine, $N^6$-isopentyl-adenine, 2-methylthio-N.sup.6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromo-guanine, 8-chloroguanine, 8-aminoguanine, 8-methylguanine, 8-thioguanine, 5-fluoro-uracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methyl-aminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

Nucleotidic analytes also include oligonucleotides, wherein the term "oligonucleotide," for purposes of the present invention, is generic to polydeoxyribo-nucleotides (containing 2-deoxy-D-ribose), to polyribonucleotides (containing D-ribose), to any other type of polynucleotide which is an N-glycoside of a purine or pyrimidine base, and to other polymers containing nonnucleotidic backbones. Thus, an oligonucleotide analyte herein may include oligonucleotide modifications, for example, substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.). There is no intended distinction in length between the terms "polynucleotide" and "oligonucleotide," and these terms are used interchangeably. These terms refer only to the primary structure of the molecule. As used herein the symbols for nucleotides and polynucleotides are according to the IUPAC-IUB Commission of Biochemical Nomenclature recommendations (Biochemistry 9:4022, 1970).

"Peptidic" analytes are intended to include any structure comprised of one or more amino acids, and thus include peptides, dipeptides, oligopeptides, polypeptides, and proteins. The amino acids forming all or a part of a peptidic analyte may be any of the twenty conventional, naturally occurring amino acids, i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y), as well as non-conventional amino acids such as isomers and modifications of the conventional amino acids, e.g., D-amino acids, non-protein amino acids, post-translationally modified amino acids, enzymatically modified amino acids, β-amino acids, constructs or structures designed to mimic amino acids (e.g., α, α-disubstituted amino acids, N-alkyl amino acids, lactic acid, β-alanine, naphthylalanine, 3-pyridylalanine, 4-hydroxyproline, O-phosphoserine, N-acetylserine, N-formyl-methionine, 3-methylhistidine, 5-hydroxylysine, and norleucine), and other non-conventional amino acids, as described, for example, in U.S. Pat. No. 5,679,782 to Rosenberg et al. Peptidic analytes may also contain non-peptidic backbone linkages, wherein the naturally occurring amide —CONH— linkage is replaced at one or more sites within the peptide backbone with a non-conventional linkage such as N-substituted amide, ester, thioamide, retropeptide (—NHCO—), retrothioamide (—NHCS—), sulfonamido (—SO$_2$NH—), and/or peptoid (N-substituted glycine) linkages. Accordingly, peptide analytes can include pseudopeptides and peptidomimetics. Peptide analytes can be (a) naturally occurring, (b) produced by chemical synthesis, (c) produced by recombinant DNA technology, (d) produced by biochemical or enzymatic fragmentation of larger molecules, (e) produced by methods resulting from a combination of methods (a) through (d) listed above, or (f) produced by any other means for producing peptides.

Saccharidic analytes include, without limitation, monosaccharides, disaccharides, oligosaccharides, polysaccharides, mucopolysaccharides or peptidoglycans (peptidopolysaccharides) and the like.

An exemplary embodiment of the invention involves replacement of a standard, relatively nonvolatile buffer salt associated with ion suppression by a substitute buffer salt that is more volatile than the standard buffer salt and provides for reduced ion suppression as evidenced by an increased analyte signal and/or an increased signal-to-noise ratio. It is established that relatively nonvolatile salts in fluid samples are frequent contaminants that can cause ion suppression and thus imprecise or incorrect results.

In this embodiment, the necessary non-analyte component is the salt component of a standard buffer system, and the substitute component is a more volatile salt that serves the same purpose, i.e., maintains the same pH, and that reduces or eliminates the ion suppression seen with the standard buffer salt. In general, salts of strong acids or bases are not sufficiently volatile for the present purpose. For instance, sodium cations, potassium cations, calcium cations, and tetrabutylammonium cations should be avoided, as should anions such as sulfates and nitrates. A notable exception is hydrochloric acid, which although a strong acid in water, is a relatively weak acid in the gas phase. Further, ions bearing multiple charges, such as sulfates, citrates and phosphates, are not likely to be volatile. Finally, higher molecular weight salts such as fatty acid salts are not likely to be volatile except at very high temperatures.

Examples of relatively volatile buffer salts that may replace the conventional buffer salts, or original non-analyte component, include, without limitation, the following:

Ammonium bicarbonate
Ammonium formate
Ammonium acetate
Ammonium propionate
Ammonium butyrate
Pyridinium formate
Pyridinium acetate
Pyridinium propionate
Pyridinium butyrate
Ethylmorpholinium acetate
Dimethylamino formate
Dimethylamino acetate
Dimethylamino propionate
Dimethylamino butyrate
Methylethylamino formate
Methylethylamino acetate
Methylethylamino propionate
Methylethylamino butyrate
Diethylamino formate
Diethylamino acetate
Diethylamino propionate
Diethylamino butyrate Within the aforementioned group, preferred volatile buffer salts include the following:

Ammonium bicarbonate
Ammonium formate
Ammonium acetate
Pyridinium acetate
Pyridinium formate
Ethylmorpholinium acetate
Trimethylamino acetate
Trimethylamino formate It is to be understood that the aforementioned salts are merely representative, and that other salts may also be used, providing that they serve the same purpose as the salt they are replacing and that they meet the volatility and enhanced signal-to-noise criteria set forth herein.

Candidate salts may be readily tested for volatility using methods well known to those of ordinary skill in the art. Such methods include, for example, a dry residue analysis, in which the candidate salt or buffer composition is placed in a volatile solvent and then heated to dryness. The presence of any dry residue suggests that the salt is not sufficiently volatile for use in the present purpose. Those candidate salts established as sufficiently volatile are then tested for their capability to reduce ion suppression, by conducting a comparison of the candidate salt with the necessary non-analyte component the candidate salt is intended to replace. Volatility may also be evaluated using butyl acetate number, a measure of relative evaporation rates, as will be appreciated by those in the field.

Generally, although not necessarily, the ionic detection device is a mass spectrometer. It will be appreciated that various volatilization techniques are available in connection with mass spectrometry, including thermal methods and electrospray, and any effective volatilization technique may be used in conjunction with the present method. Any of a number of known ionization means may also be used, including chemical ionization, field desorption ionization, electrospray ionization, atmospheric pressure chemical ionization, matrix-assisted laser desorption ionization, and inductively coupled plasma ionization, and, again, any effective ionization technique may be advantageously employed herein. Depending on the nature of the analyte, mass spectrometric measurements can be performed in negative or positive mode, with acidic analytes preferentially ionizing in the negative mode and basic analytes preferentially ionizing in the positive mode.

In a preferred embodiment, the improved method of the invention employs acoustic ejection to produce very small droplets that are then volatilized, ionized, and analyzed. These small droplets are nanoliter-sized droplets, defined herein as a droplets containing at most about 5 nl of fluid sample, preferably not more than about 2.5 nl, more preferably less than 1 nl, most preferably smaller than about 50 pl, and optimally less than about 1 pl. Acoustic ejection of droplets from the surface of a fluid sample is effected using an acoustic ejector as will be described in detail below. Acoustic ejection technology is particularly suited to high-throughput mass spectrometry (HTMS), insofar as HTMS has been hampered by the lack of easily automated sample preparation and loading, the need to conserve sample, the need to eliminate cross contamination, the inability to go directly from a fluid reservoir into the analytical device, and the inability to generate droplets of the appropriate size.

The present method has proved to be unexpectedly effective with nanoliter-sized droplets, as seen in the Examples herein. It is well understood that fundamental fluid physics changes as the size scale is decreased, i.e., as fluid droplets become smaller and smaller. Otherwise applicable principles of diffusion and mixing tend not to apply to nanoliter-sized droplets, nor are conventional analyses workable when attempting to predict the flow dynamics of an element, ion, or compound moving from the interior of a nanoliter-sized droplet to the droplet surface, e.g., for purposes of volatilization.

Acoustic ejection of droplets that are then volatilized provides numerous advantages. In volatilizing droplets that are nanoliter-sized, e.g., using a thermal volatilization technique, the large surface area of these small droplets facilitates the gas phase extraction of the relatively volatile substitute component, leaving behind the charged analyte in the evaporating droplet. Thus, by enabling gas phase extraction of the substitute component, e.g., the substitute buffer salt or the like, acoustic ejection eliminates the need for liquid phase or solid phase "clean up" of a fluid sample to remove interfering components that cause ion suppression. This significantly increases the number of samples that can be analyzed using mass spectrometry or the like in a given period of time. With current commercially available methodology, the need for an additional step to remove buffer, other salts, detergents, and any other non-analyte species results in a processing time in the range of 7-20 seconds per sample, while the present invention enables processing time of well under 1 second per sample, typically on the order of about 0.3 seconds per sample. Combining this feature with the fact that the present process can be carried out using far smaller sample sizes and with the fact that the analyte signal obtained is increased by virtue of the gas phase extraction step means that the invention enables a far more rapid, economical, and accurate method for analyzing fluid samples using mass spectrometry or other ionic detection devices.

Acoustic ejection, as noted above, enables rapid sample processing as well as generation of nanoliter-sized droplets of predetermined and consistent size; see U.S. Pat. No. 6,416,164 to Stearns et al., cited and incorporated by reference earlier herein. The aforementioned patent describes how the size of acoustically ejected droplets from a fluid surface can be carefully controlled by varying the acoustic power, the acoustic frequency, the toneburst duration, and/or the F-number of the focusing lens. An additional advantage of using acoustic ejection in conjunction with the present invention is that droplets can be ejected from a very small sample size, on the order of 5 µl or less. This is particularly advantageous when sample availability is limited and a small fluid sample must be analyzed out of necessity. In terms of processing capability, U.S. Pat. No. 6,938,995 to Mutz et al. explains that acoustic ejection technology, used in conjunction with acoustic assessment of fluid samples in a plurality of reservoirs, can achieve analysis of over 5, 10, or even 25 reservoirs per second, translating to well in excess of 50,000 fluid samples per day.

In one embodiment, then, the improved method of the invention makes use of an acoustic ejector as a fluid sample droplet generation device, the device including at least one reservoir to contain the fluid sample, an acoustic ejector, and a means for positioning the acoustic ejector in acoustic coupling relationship with the reservoir. Typically, a single ejector is used that is composed of an acoustic radiation generator and a focusing means for focusing the acoustic radiation generated by the acoustic radiation generator. However, a plurality of ejectors may be advantageously used as well. Likewise, although a single reservoir may be used, the device typically includes a plurality of reservoirs.

Examples of acoustic ejection devices useful in conjunction with the present invention are described in detail in U.S. Pat. No. 6,802,593 to Ellson et al., U.S. Pat. No. 7,270,986 to Mutz et al., U.S. Pat. No. 7,439,048 to Mutz et al., and U.S. Pat. No. 6,603,118 to Ellson et al., incorporated by reference herein. As described therein, an acoustic ejection device may be constructed to include multiple reservoirs as an integrated or permanently attached component of the device. However, to provide modularity and interchangeability of components, it is preferred that device be constructed with removable reservoirs. Generally, the reservoirs are arranged in a pattern or an array to provide each reservoir with individual systematic addressability. In addition, while each of the reservoirs may be provided as a discrete or stand-alone item, in circumstances that require a large number of reservoirs, it is preferred that the reservoirs be attached to each other or represent integrated portions of a single reservoir unit. For example, the reservoirs may represent individual wells in a well plate. Many well plates suitable for use with the device are commercially available and may contain, for example, 96, 384, 1536, or 3456 wells per well plate, having a full skirt, half skirt, or no skirt. Well plates or microtiter plates have become commonly used laboratory items. The Society for Laboratory Automation and Screening (SLAS) has established and maintains standards for microtiter plates in conjunction with the American National Standards Institute, including the footprint and dimension standards ANSI/SLAS 1-2004. The wells of such well plates typically form rectilinear arrays.

However, the availability of such commercially available well plates does not preclude the manufacture and use of custom-made well plates in other geometrical configurations containing at least about 10,000 wells, or as many as 100,000 to 500,000 wells, or more. Furthermore, the material used in the construction of reservoirs must be compatible with the fluid samples contained therein. Thus, if it is intended that the reservoirs or wells contain an organic solvent such as acetonitrile, polymers that dissolve or swell in acetonitrile would be unsuitable for use in forming the reservoirs or well plates. Similarly, reservoirs or wells intended to contain DMSO must be compatible with DMSO. For water-based fluids, a number of materials are suitable for the construction of reservoirs and include, but are not limited to, ceramics such as silicon oxide and aluminum oxide, metals such as stainless steel and platinum, and polymers such as polyester, polypropylene, cyclic olefin copolymers (e.g., those available commercially as Zeonex® from Nippon Zeon and Topas® from Ticona), polystyrene, and polytetrafluoroethylene. For fluids that are photosensitive, the reservoirs may be constructed from an optically opaque material that has sufficient acoustic transparency for substantially unimpaired functioning of the device.

In addition, to reduce the amount of movement and time needed to align the acoustic radiation generator with each reservoir or reservoir well during operation, it is preferable that the center of each reservoir be located not more than about 1 centimeter, more preferably not more than about 1.5 millimeters, still more preferably not more than about 1 millimeter and optimally not more than about 0.5 millimeter, from a neighboring reservoir center. These dimensions tend to limit the size of the reservoirs to a maximum volume. The reservoirs are constructed to contain typically no more than about 1 mL, preferably no more than about 1 µL, and optimally no more than about 1 nL, of fluid. To facilitate handling of multiple reservoirs, it is also preferred that the reservoirs be substantially acoustically indistinguishable.

A vibrational element or transducer is used to generate acoustic radiation. In some instances, the acoustic radiation generator is comprised of a single transducer. In addition, the transducer may use a piezoelectric element to convert electrical energy into mechanical energy associated with acoustic radiation. Alternatively, multiple element acoustic radiation generators such as transducer assemblies may be used. For example, linear acoustic arrays, curvilinear acoustic arrays or phased acoustic arrays may be advantageously used to generate acoustic radiation that is transmitted simultaneous to a plurality of reservoirs.

An added element in the form of a gas phase extraction device thermally volatilizes droplets ejected using an acoustic radiation generator as just described, and extracts unwanted species from the droplets prior to analysis using, e.g., a mass spectrometer. Replacement of conventionally used components with more volatile substitutes (e.g., buffer salts) or substitutes that undergo a chemical reaction to provide volatile species, facilitates ready gas phase extraction of these components, thus eliminating or at least substantially reducing ion suppression or other types of interference seen with the conventional compounds.

As noted earlier herein, the method of the invention employs a substitute component for the original non-analyte component that serves the same purpose as the original component but is either (1) more volatile than the original component and/or the analyte or (2) undergoes a chemical reaction upon volatilization to yield a reaction product that is more volatile than the original component and/or the analyte. Embodiment (1) is discussed above. Now turning to embodiment (2), the substitute component is in this case not necessarily more volatile than the original component and/or the analyte, but is rather selected to undergo a chemical reaction that yields at least one volatile reaction product. The substitute component may be a zwitterionic compound that undergoes an intramolecular conversion, as will be discussed in detail below, or the substitute component may be a nonzwitterionic compound that can be chemically cleaved to yield a volatile reaction product. Alternatively, the substitute component may be a compound that undergoes a thermally induced reaction to give rise to at least one volatile reaction product. The compound may also be selected to undergo a photocatalytic reaction that results in at least one volatile reaction product, where, it is to be understood, the term "volatile reaction product" refers to a reaction product that is more volatile than the original component and/or the analyte.

Zwitterionic Compound as the Substitute Component:

When a zwitterionic compound is used as the substitute component, e.g., as a buffer salt in a fluid sample requiring a buffer system, the zwitterionic compound is selected so as to undergo a chemical reaction at elevated temperature and/or under reduced pressure during the volatilization process, to provide at least one reaction product that is more volatile than the original non-analyte component and/or the analyte. The zwitterionic compounds described infra are useful in other methods as well, e.g., in any method that involves ionization and volatilization of a buffered fluid sample followed by detection of the analyte in the ionized and volatilized sample.

By "zwitterion" or a "zwitterionic" compound as those terms are used herein is meant a compound that contains a pair of ionizable groups, one that ionizes to form a positively charged species and the other that ionizes to form a negatively charged species. The former is typically a nitrogen atom-containing group such as a substituted or unsubstituted amine or a diazo substituent, and the latter is generally although not necessarily a carboxyl (COOH) substituent. It will be appreciated that at higher pH values only the nitrogen atom-containing group will bear a charge, such that the compound is cationic, while at lower pH values only the carboxyl-containing group will be ionized, such that the compound is anionic. At intermediate pH values, generally in the range of about 5 to about 8, both entities bear a charge and it is in this form that the reactions described below proceed in an optimal manner.

In one embodiment, the zwitterionic compound is a partially unsaturated compound, i.e., a compound that contains at least one unsaturated bond, such as a double bond, and is "pre-aromatic" in the sense that the intramolecular decomposition results in the generation of a volatile aromatic compound. For instance, the partially unsaturated, pre-aromatic zwitterionic compound may comprise a partially unsaturated, pre-aromatic core to which a carboxylic acid group (—COOH) and a nitrogen-containing substituent are covalently bound, wherein the nitrogen-containing substituent may be selected from amino, primary amino, secondary amino, tertiary amino, and diazo. In this example, the carboxylic acid group and the nitrogen-containing substituent are positioned with respect to each other so that the intramolecular decomposition yields a volatile aromatic compound (i.e., an aromatic compound that is more volatile than the original component and/or the analyte), releases carbon dioxide, and generates a nitrogen-containing compound such as ammonia, a substituted or unsubstituted amine (generally gaseous), or nitrogen gas. The pre-aromatic core is generally cyclic, although an acyclic core is suitable provided that the aforementioned intramolecular decomposition reaction results in a volatile compound, preferably a volatile aromatic compound, in addition to release of carbon dioxide and a nitrogen-containing compound. This pre-aromatic zwitterionic compound containing pre-aromatic core Q and the nitrogen-containing substituent N* may be represented by structure (1)

(1)

When the core Q is cyclic, transformation from the pre-aromatic compound can occur according to the following scheme (I) when the carboxylate group and the N* substituent are bound to adjacent carbon atoms in a ring:

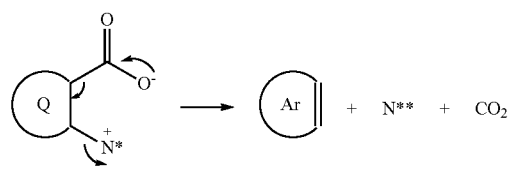
(I)

In Scheme (I), Ar represents the volatile aromatic reaction product, and each N** reaction product corresponds to each N* substituent. This reaction may be illustrated using a more specific example in which, solely for purposes of illustration, the core Q comprises a cyclohexa-1,3-diene ring, such that, as shown in Scheme (II), the volatile aromatic reaction product is benzene:

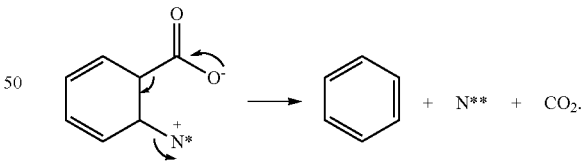
(II)

The N* substituent, in cationic form, may be, for instance, —$(NH_3)^+$, —$(NHR^1)^+$, $(NR^2R^3)^+$, $(NR^4R^5R^6)^+$, or diazo, such that the N will be, respectively, ammonia ($NH_3$), $NH_2R^1$, $NHR^2R^3$, $NR^4R^5R^6$, or nitrogen gas ($N_2$). $R^1$ through $R^6$ are non-hydrogen substituents such as lower alkyl, i.e., a $C_1$-$C_6$ alkyl group, preferably a $C_1$-$C_3$ alkyl group, that may or may not be substituted with substituents that will not interfere in the detection process or interact with any of the components of the sample in a deleterious manner. The decomposition reaction thus results in two products that will not be detected, i.e., the volatile aromatic compound and carbon dioxide, and to the nitrogenous species N which, is unlikely to cause ion suppression.

In Scheme (II), the cyclohexa-1,3-diene reactant may or may not be substituted with one or more ring substituents that do not interfere with the chemical reaction shown or with any other compounds that are present, and are generally selected from the same group of substituents as $R^1$ through $R^6$, and the carboxylate and cationic nitrogen-containing substituent that are shown as ortho to each other may be in either cis or trans relationship (compound (2))

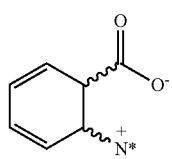

(2)

but are preferably in the trans configuration (compound (3)):

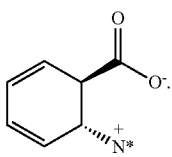

(3)

The optionally present substituents are illustrated in structure (4)

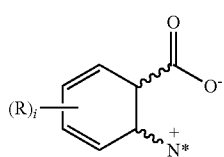

(4)

in which, as shown, there are i substituents where i is in the range of zero to 6 inclusive, wherein the substituents, represented as R, may be the same or different. In one particular case, wherein N* is diazo, it is preferred that the carboxylate and diazo substituent are in the trans position with a substituent attached to the same carbon as the diazo group, where that substituent, shown as $R^7$ in compound (5), is $C_1$-$C_6$ alkyl, preferably $C_1$-$C_3$ alkyl (omission of $R^7$ results in a compound that is too unstable for the present purpose):

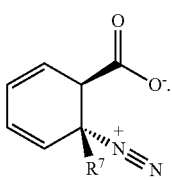

(5)

In a related embodiment, the zwitterionic compound is an aromatic compound substituted with a carboxylate group and a diazo group, such as ortho-diazo benzoic acid, in which case the intramolecular reaction results in the N** reaction product benzyne (Scheme (III)):

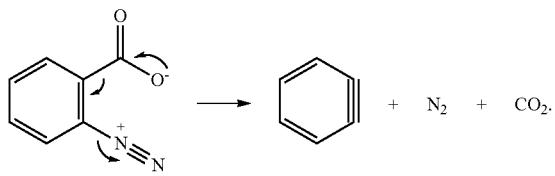

(III)

Benzyne is a very reactive compound that will serve as an intermediate to further reaction. In this case, a second reactant, e.g., water, or a diene, is introduced into the sample to react with benzyne. Water will result in reaction to give phenol, while proper selection of the diene, as will be understood by a skilled practitioner, will yield a volatile reaction product. As one example, furan may serve as the diene, in which case reaction with benzyne gives the volatile product 1,2,3,4-tetrahydro-1,4-epoxynaphthalene. As another example, anthracene may serve as the diene, resulting in the volatile reaction product triptycene.

The zwitterionic compound may be cyclic or acyclic, and, if cyclic, it may be monocyclic, bicyclic, or polycyclic, and may contain aromatic rings as well as a molecular segment that is only partially unsaturated. When the chemical reaction of the zwitterionic compound results in a volatile aromatic compound as a reaction product, this is generally, although not necessarily, by addition of a double bond to a ring structure to generate 4n+2 aromaticity. Examples include addition of a double bond to a substituted or unsubstituted cyclohexyl-1,3-dienyl ring to generate a benzene ring, or addition of a double bond to a substituted or unsubstituted dihydrofuran ring to generate furan, an aromatic. Thus, the zwitterionic compound may, in one instance, comprise a cyclohexyl-1,3-dienyl core that is substituted with the —COOH and —N* moieties at adjacent carbon atoms, such that the compound comprises 5-carboxyl-6-N*-cyclohexa-1,3-diene, e.g., 5-carboxyl-6-amino-cyclohexa-1,3-diene, which may be further substituted as indicated above, and which converts to a substituted or unsubstituted benzene ring following reaction. A further zwitterionic compound may comprise a cyclohexa-1,4-diene core substituted with —COOH and —N* in the para configuration, such that the compound is or contains 3-carboxyl-6-N*-cyclohexa-1,4-diene, either unsubstituted or substituted as above, which converts via the decomposition reaction to a substituted or unsubstituted benzene ring. Another zwitterionic compound may comprise, for instance, dihydrofuran substituted at the 2-position and 3-position with the —COOH and —N* moieties, such that the compound comprises 2-carboxyl-3-N*-2,3-dihydrofuran or 2-N*-3-carboxyl-2,3-dihydrofuran, either unsubstituted or unsubstituted as described earlier herein, which, upon reaction, converts to substituted or unsubstituted furan, an aromatic molecule.

Specific examples of these zwitterionic compounds include, without limitation, the following (for simplicity, the compounds are shown in uncharged form; it will be understood, however, that at intermediate pH values each compound will contain both an anionic species and a cationic species, i.e., a carboxylate group —COO⁻ and a positively charged nitrogen atom):

6-Amino-3,4-dimethylcyclohexa-2,4-diene-1-carboxylic acid:

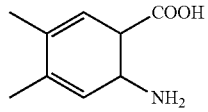
(6)

1,6-Diamino-2,4-diene-1-carboxylic acid:

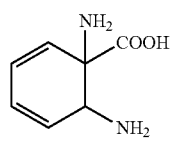
(7)

6-Amino-1,4-dimethylcyclohexa-2,4-diene-1-carboxylic acid:

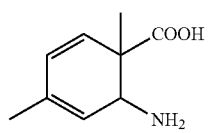
(8)

6-Aminocyclohexa-2,4-diene-1-carboxylic acid:

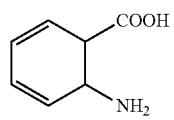
(9)

6-(Dimethylamino)cyclohexa-2,4-diene-1-carboxylic acid:

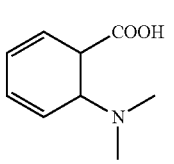
(10)

6-(Ethylamino)cyclohexa-2,4-diene-1-carboxylic acid:

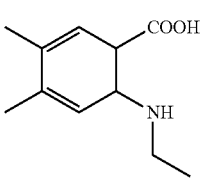
(11)

3-Amino-2,3-dihydrofuran-2-carboxylic acid:

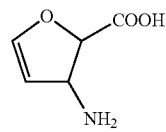
(12)

4-Aminocyclohexa-2,5-dienecarboxylic acid:

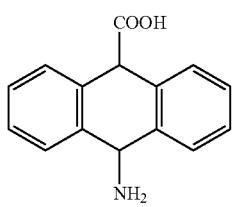
(13)

10-Amino-9,10-dihydroanthracene-9-carboxylic acid:

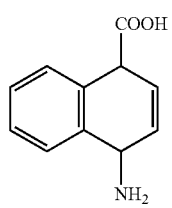
(14)

4-Amino-1,4-dihydronaphthalene-1-carboxylic acid:

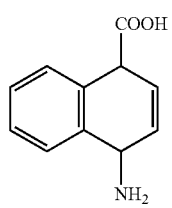
(15)

2-Amino-1,2-dihydronaphthalene-1-carboxylic acid:

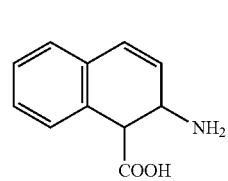
(16)

2-Amino-1,2-dihydronaphthalene-1-carboxylic acid:

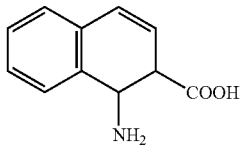

(17)

4-(Ethylamino)-1,4-dihydronaphthalene-1-carboxylic acid:

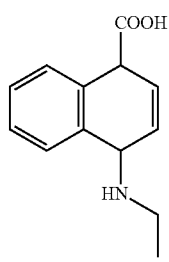

(18)

These zwitterionic compounds may be obtained commercially or synthesized using methods known in the art and described in the pertinent literature. Carboxylate-containing zwitterions can be synthesized using any of a variety of techniques for combining a carboxyl-containing compound with an amine or other nitrogenous compound. Zwitterionic sulfonic acid-containing compounds such as zwitterionic detergents and buffers can generally be synthesized from substituted or unsubstituted 1,2-oxathiolane-2,2-dioxide and a substituted or unsubstituted amine, according to Scheme (IV):

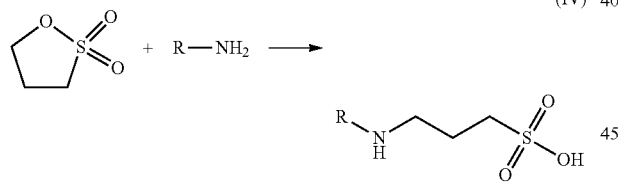

(IV)

Other Chemically Cleavable Substitute Components:

Alternatively, a chemically cleavable nonzwitterionic compound can be selected to serve as the substitute component, wherein the chemically cleavable compound contains at least one linkage that can be cleaved with an acid, base, or other reagent. Representative linkages hydrolytically cleavable in the presence of acids or bases include the following: carboxylate ester (—(CO)—O—); enol ether (—CH=CH—O—); acetal (—O—CR$_2$—O—); hemiacetal (—CH(OH)—O—); anhydride (—(CO)—O—(CO)—); carbonate (—O—(CO)—O—); amide ((—(CO)—NH—); N-substituted amide (—(CO)—NR—); urethane (—O—(CO)—NH—); N-substituted urethane (—O—(CO)—NR—); imido (—CH=N—); N,N-disubstituted hydrazo (—NR—NR—); thioester (—(CO)—S—); phosphonic ester (—P(O)(OR)—O—); sulfonic ester (—SO$_2$—OR—); ortho ester (—C(OR)$_2$—O—); and betaine ester (R—O—(CO)—N(W)$_4^+$X$^-$ where the R' may be the same or different non-hydrogen substituents and X is the associated counterrion). Other chemically cleavable linkages include, without limitation: the hydroxylamine-cleavable linkage —(CO)—O—CH$_2$—CH$_2$—O—(CO)—; the thiol-cleavable linkage —S—S, also cleavable upon treatment with trisubstituted phosphines such as triphenylphoephine; periodate cleavable cis-diols —CH(OH)—CH)OH—; and the fluoride-cleavable linkage —(O)—NH—(CH$_2$)$_2$—O—(CH$_2$)$_2$—O—(CH$_2$)$_2$—(NH)—(CO)—. Surfactants containing chemically cleavable linkages have been described, along with synthesis thereof these include ProteaseMAX (V2071) (Promega); RapiGest SF (Waters); PPS Silent Surfactant (Agilent); MaSDeS (see Chang et al. (January 2015) *J. Proteome Res.* 14(3)); Invitrosol (Life Technologies, Inc.); Progenta AALS I (sodium 2,2-dihexoxypropyl sulfate, from Protea Biosciences); Progenta AALS II (sodium 2,2-diheptoxypropyl sulfate, also from Protea Biosciences); Progenta CALS I (2,2-dihexoxypropyl ammonium bromide, also from Protea Biosciences); and Progenta CALS II (2,2-diheptoxypropyl ammonium bromide, also from Protea Biosciences). These surfactants and analogs thereof can be used advantageously in the present compositions, as can buffers and other compounds containing these and other chemically cleavable linkages.

Thermally Cleavable Substitute Components:

Substitute components can also contain linkages that are cleavable with heat, such that they serve the same purpose as the original component in the fluid sample but cleave into smaller compounds upon volatilization of the sample, where those smaller compounds are either volatile or unlikely to cause ion suppression. Thermally cleavable linkages include ester linkages, carbamate linkages, carbonate linkages, urethane-type linkages (—O—(CO)—NH—) and N-substituted urethane linkages (—O—(CO)—NR—) in which the nitrogen atom of the linkage is substituted with a non-hydrogen substituent such as lower alkyl. Other thermally cleavable linkages include furan-maleimide Diels-Alder adducts (see Szalal et al. (2007) *Macromolecules* 40(4): 818-823), oxirane and thiirane-based linkages, and ester-substituted sulfones that thermally decompose to an ester and gaseous SO$_2$ according to the following scheme

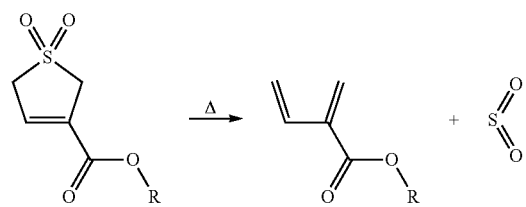

(V)

wherein R is a nonhydrogen substituent, generally an alkyl group (e.g., piperylene, as described by Eckert and Liotta, "Designing Smart Surfactants" printed from www.chbe.gatech.edu/eckert/pdf/-surfactant.pdf, Internet site accessed on Oct. 19, 2015).

Photolytically Cleavable Substitute Components:

Incorporation of one or more photolytically cleavable sites into the substitute component allows for irradiation-induced cleavage prior to introduction of the sample into the mass spectrometer or other analytical device. The sample fluid or fluids can be irradiated in the gas phase, i.e., after fluid droplet ejection but prior to entry into the mass spectrometer, or they may be irradiated in the liquid phase, e.g., in a well plate or other container or group of containers. Irradiation in the gas phase enables real-time conversion to the cleavage products, while irradiation in the liquid phase, where sample fluid is present in a multiplicity of containers or wells, does not.

Photolytically cleavable sites can be readily incorporated into the substitute component, e.g., the buffer, surfactant, or the like, using synthetic organic techniques known to those of ordinary skill in the art and/or described in the pertinent texts and literature. One type of photolytically cleavable linkage is composed of an ortho-nitrobenzyl group as in the following representative structure

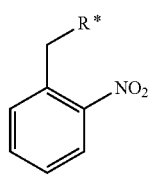
(19)

where R* is generally a nitrogen atom or oxygen atom bound to the rest of the molecule. Such structures thus include

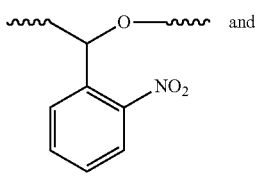
(20)

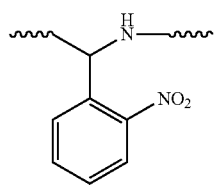
(21)

as well as the N-substituted analog

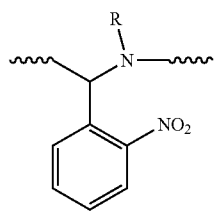
(22)

in which R, again, is a non-hydrogen substituent such as lower alkyl, and the ∿∿ symbol represents attachment to the remainder of the molecule. Another photolytically cleavable linkage includes, by way of example, the cinnamic acid-type linkage

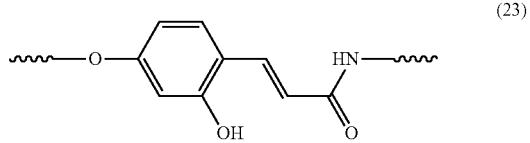
(23)

described, for example, by Sakai et al. (15 Jun. 2012) J. Colloid and Interface Sci. 376(1):160-164, with respect to the photocleavable surfactant

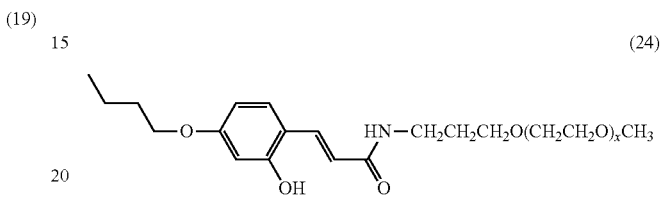
(24)

Other photolytically cleavable linkages include benzyl ethers (which cleave to form alcohols), carbamate linkages (which cleave to form amines), 1,3-dithiane linkages (which cleave to form carbonyl groups); ortho-nitroanilide linkages (which cleave to form carboxyl groups), benzoin-type linkages (which cleave to form phosphate groups), and the like. See, e.g., Pelliccioli et al. (2002) Photochem. Photobiol. Sci. 1:441-458, and Greene et al., Protective Groups in Organic Synthesis, $3^{rd}$ edition, John Wiley & Sons (New York, N.Y.: 1999).

Those of ordinary skill in the art will be able to use known methods of organic synthesis and/or methods described in the literature to synthesize suitable zwitterionic and/or cleavable compounds that can be used as the substitute component herein. Additionally, known buffers (e.g., the Good's buffers; see Good et al. (1966) Biochemistry 5(2): 467-477), surfactants, and the like may be modified to incorporate such cleavable linkers.

One representative buffer of interest is the acetal-containing compound (25)

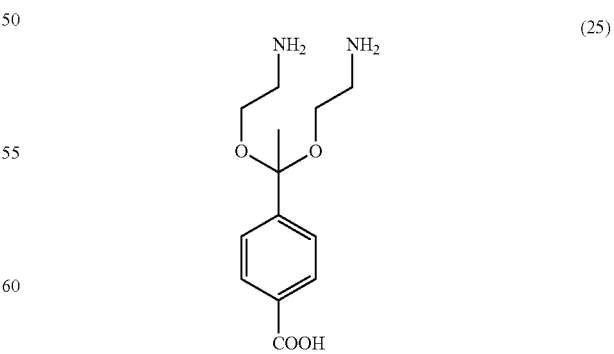
(25)

which decomposes photolytically and/or in the presence of acid as follows to give 2-aminoethanol and 2-formylbenzoic acid. Another buffer of interest is compound (26)

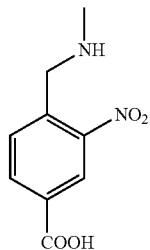

(26)

which can be photolytically cleaved to give methamine (CH$_3$—NH$_2$) and 4-formyl-3-nitrosobenzoic acid.

Compounds having the general structure

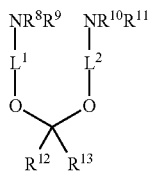

(27)

are suitable substitute components herein, particularly as an acid-cleavable buffer. In (27), L$^1$ and L$^2$ are C$_1$-C$_6$ hydrocarbyl linkages, generally C$_2$-C$_4$ hydrocarbyl, R$^8$, R$^9$, R$^{10}$, and R$^{11}$ are independently selected from H and C$_1$-C$_{16}$ hydrocarbyl (e.g., alkyl, cycloalkyl, alkenyl, etc., particularly lower alkyl), R$^{12}$ is lower alkyl, and R$^{13}$ is either —COOH or —CH$_2$OSO$_3$H. When R$^{13}$ is —COOH, the compound may be represented as (28), while when R$^{13}$ is —CH$_2$OSO$_3$H, the compound may be represented as (29):

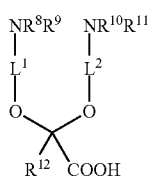

(28)

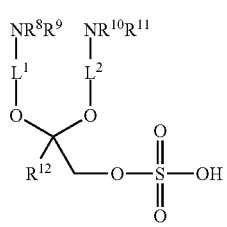

(29)

In a preferred embodiment, R$^8$, R$^9$, R$^{10}$, and R$^{11}$ are H, L$^1$ and L$^2$ are —CH$_2$CH$_2$—, and R$^{12}$ is methyl, such that generic compounds (28) and (29) have the structures (30) and (31), respectively:

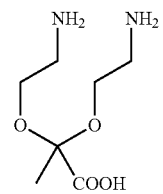

(30)

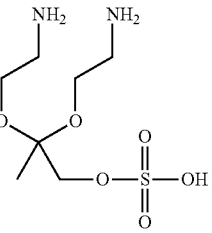

(31)

Figure 4:
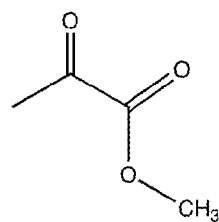
FIG. 4 schematically illustrates the synthesis of cleavable buffer compound (30).
Figure 4:
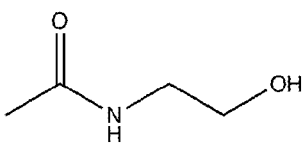
Figure 4:
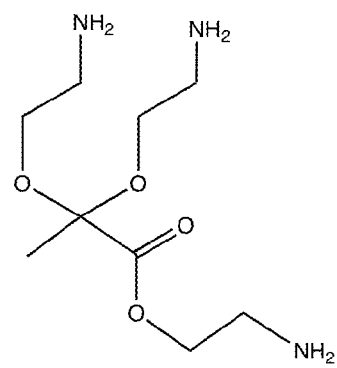
Figure 4:
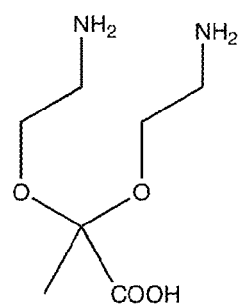
Figure 5:
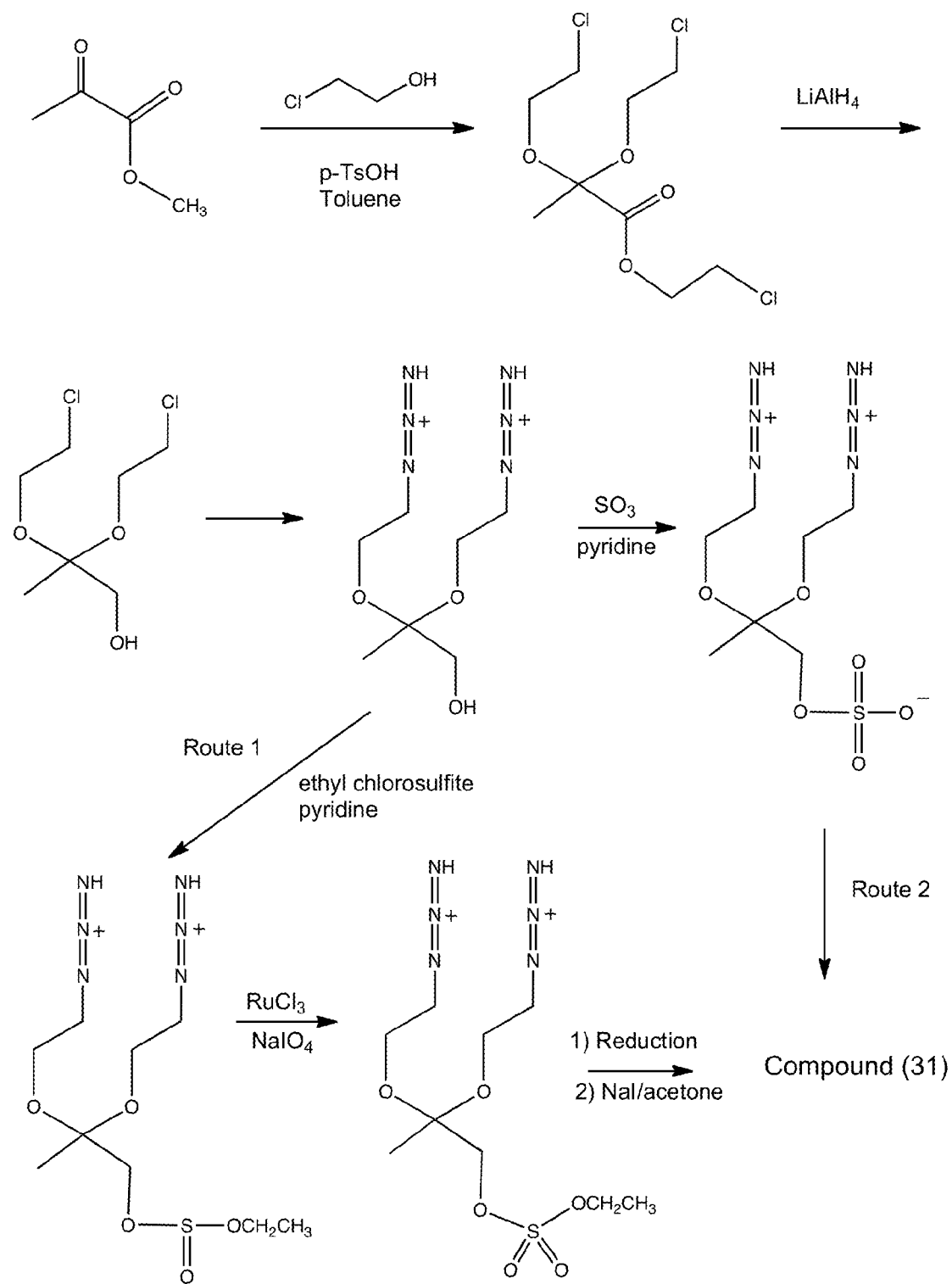
FIG. 5 schematically illustrates the synthesis of cleavable buffer compound (31), using two alternate routes.

Both compounds can be synthesized from methyl pyruvate. Compound (30) has a pI of approximately 9.44 and is optimally employed as a buffer at a pH in the range of approximately 7.5 to 10.5. Compound (31) has a pI of approximately 9.44 and is optimally employed as a buffer at a pH in the range of approximately 8.0 to 11.0. FIG. 4 schematically illustrates the synthesis of compound (30), while FIG. 5 schematically illustrates the synthesis of compound (31). Implementation of the individual reaction steps shown therein will be within the purview of those skilled in the art and/or will become apparent upon reference to an analogous reaction in the texts or literature.

It is to be understood that while the invention has been described in conjunction with a number of specific embodiments, the foregoing description as well as the examples that follow are intended to illustrate and not limit the scope of the invention. Other aspects, advantages and modifications will be apparent to those skilled in the art. All patents, patent applications, and publications mentioned here are hereby incorporated by reference in their entireties.

Example 1

In this example, the impact of buffer volatility on the mass spectrometric determination of caffeine was evaluated using ammonium acetate as a volatile buffer salt and sodium chloride as a nonvolatile buffer salt. Fluid samples were prepared with varying concentrations of either ammonium acetate or sodium chloride, at 1 mM, 2 mM, 5 mM, 10 mM, 25 mM, 50 mM, 100 mM, 250 mM, and 500 mM. Sample droplets were generated using a modified Echo® 555 liquid handler (Labcyte Inc., Sunnyvale, Calif.). The instrument was modified to move the transducer assembly to the exterior of the instrument underneath a nozzle to allow the droplet stream to be exposed to 195° C. heat, thus enabling gas phase extraction of volatile salt, and pulled into a beta version of the SQ Detector II mass spectrometer (Waters Micromass).

FIG. 1 is a plot of normalized signal at m/z=195 versus ammonium acetate (♦) or sodium chloride (■) concentration (mM). As may be seen, the concentration of caffeine detected decreases rapidly at even low sodium chloride concentrations, a phenomenon not seen with ammonium acetate. This result indicates that the more volatile buffer salt allows for analyte detection, even at higher buffer salt concentrations, while the less volatile buffer salt does not.

Experimental for Examples 2 and 3

All samples were analysed on a Waters SQ Detector 2 mass spectrometer fitted with a standard electrospray source running a source block temperature of 80° C., a desolvation temperature of 250° C. and a gas flow rate of 400 liters/hr. The electrospray probe voltage was set to 3500 V and the sample cone to 25 V. All samples were introduced using a Harvard 22 syringe pump fitted with a Hamilton 250 µl syringe operating at 6 µl/min. All reagents were purchased from Sigma Aldrich as dry powders except HEPES (4-(2-hydroxyethyl)-1-piperazineethanesulfonic acid, a zwitterionic buffer), which was supplied as a 1M solution. 1M stock solutions were prepared for each of the salts using HPLC grade water and a caffeine stock solution of 2 mg/ml, again in HPLC grade water. Serial dilutions were performed on each of the salt stock solutions to generate 1 mM, 5 mM, 25 mM and 50 mM working solutions. To 1 ml of each of these working solutions 50 µl of the caffeine stock solution was added to produce a 10 µg/ml caffeine solution for analysis. For each sample a syringe infusion was performed and the absolute ion signal heights for the M+H and M+Na peaks of caffeine (at 195 Da and 217 Da) were summed and plotted. Between each sample, the syringe and probe were flushed with water to remove any salt residues.

Example 2

Figure 2:
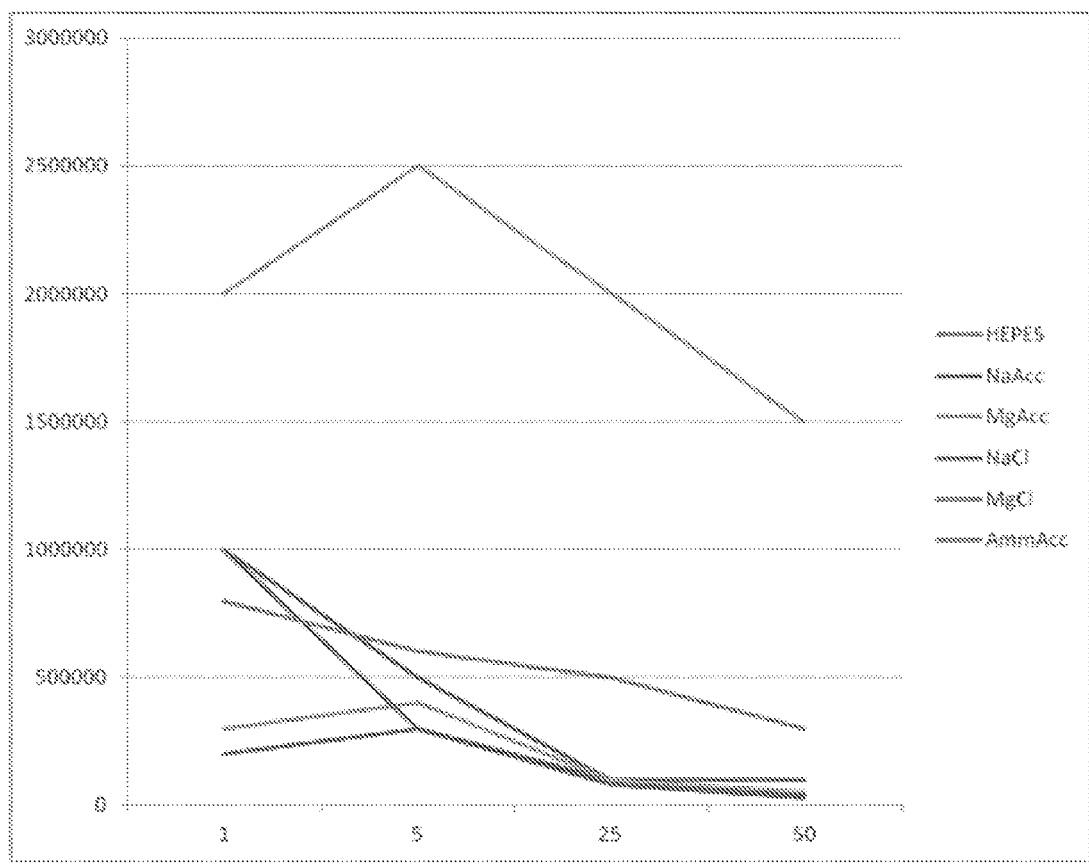
FIG. 2 is a plot of signal intensity for detected caffeine analyte versus salt concentration for six different buffer salts, as described in Example 2.

This example describes an additional evaluation of the impact of buffer volatility on the mass spectrometric determination of caffeine, with magnesium acetate used as a volatile buffer salt and magnesium chloride as a nonvolatile buffer salt. The signal intensity of caffeine and its sodium adduct was evaluated in four concentrations of six salt systems. The data, plotted in FIG. 2, shows that standard ESI system sensitivity is heavily impacted by non-volatile salts and less impacted by a volatile salt, at similar concentrations. That is, the uppermost data points in the plot correspond to the signal obtained with fluid samples containing caffeine and ammonium acetate as a buffer salt. The experiment may be repeated to carry out mass spectrometric determinations of other analytes with substantially the same results.

Example 3

Figure 3:
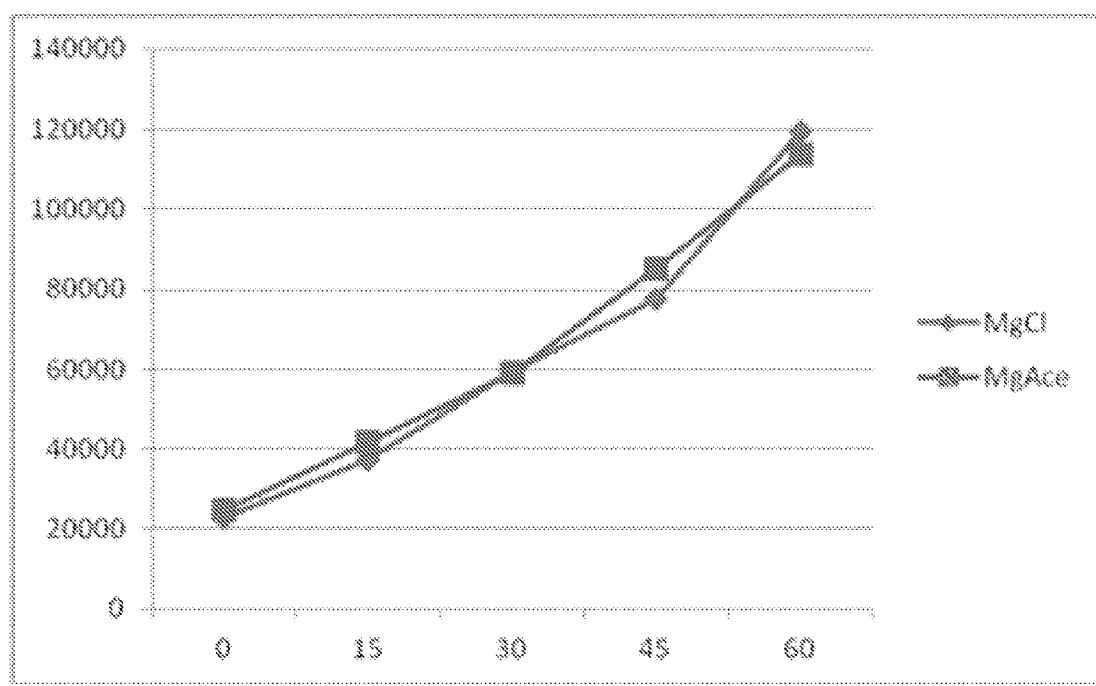
FIG. 3 is a plot of luminescence versus time for the kinase assay carried out in Example 3, conducted using a volatile magnesium salt (magnesium acetate) and, for purposes of comparison, a nonvolatile magnesium salt (magnesium chloride).

In this example, a kinase assay was conducted in which magnesium is required by the enzyme used, and the assay measures the increase in concentration of a phosphorylated peptide substrate with time. One set of samples was formulated with magnesium chloride, a relatively nonvolatile compound, and a second set of samples was formulated with magnesium acetate, a more volatile compound. The assay results using each type of magnesium salt are illustrated in FIG. 3, in which time, in minutes, is represented on the X-axis, and luminescence is represented on the Y-axis. The graph comparing results obtained for the assay employing magnesium chloride (♦) with those obtained for the assay employing magnesium acetate (■) show that the assay was not hindered or biased by the source of magnesium ions.

In many assay systems, certain non-volatile and/or highly electronegative buffer components are used; however, these components are not unique creating the biological or chemical outcome of the desired assay. The switch does not show any significant change in results for the range of up to 60 as this is within the noise of the measurement. From the previous examples for measurement of analyte with the absence of the non-volatile analyte, this assay system would provide improved results with gas phase extraction prior to MS loading due to reduce ion suppression in the analyte.

We claim:

1. An improved method for determining the concentration of an analyte in a fluid sample that additionally comprises a necessary non-analyte original component, the method comprising volatilizing and ionizing the sample, and introducing the ionized, volatilized sample into an ionic analyte detection device that provides a signal proportional in intensity to the quantity of ionized analyte detected,
   wherein the improvement comprises substituting for the necessary non-analyte original component a substitute component that:
   (a) functions as the original component in the fluid sample;
   (b) upon volatilizing the fluid sample, undergoes a decomposition reaction to yield at least one aromatic reaction product that is more volatile than the necessary original component, the analyte, or both the necessary original component and the analyte; and
   (c) results in an increase in the intensity of the signal and/or a greater signal-to-noise ratio than either the signal intensity or signal to noise ratio obtained using the original component.

2. The method of claim 1, wherein the improvement further comprises generating nanoliter-sized droplets of fluid sample prior to volatilization and ionization, such that the fluid sample is introduced into the ionic analyte detection device in the form of nanoliter-sized droplets.

3. The method of claim 2, wherein the nanoliter-sized droplets of fluid sample have a mean droplet size of less than about approximately 5 nl.

4. The method of claim 3, wherein the nanoliter-sized droplets of fluid sample have a mean droplet size of less than about approximately 2.5 nl.

5. The method of claim 4, wherein the nanoliter-sized droplets of fluid sample have a mean droplet size of less than about approximately 50 pl.

6. The method of claim 5, wherein the nanoliter-sized droplets of fluid sample have a mean droplet size of less than about approximately 1 pl.

7. The method of claim 6, wherein the acoustic ejection is carried out using an acoustic ejector that directs focused acoustic energy into a reservoir containing the fluid sample in a manner that results in the rapid ejection of consistently sized fluid droplets from the surface of the fluid sample.

8. The method of claim 2, wherein the improvement further includes using acoustic ejection to generate the nanoliter-sized droplets of the fluid sample.

9. The method of claim 1, wherein the ionic analyte detection device comprises a mass spectrometer.

10. The method of claim 9, wherein the ionizing comprises chemical ionization, field desorption ionization, electrospray ionization, atmospheric pressure chemical ionization, matrix-assisted laser desorption ionization, or inductively coupled plasma ionization.

11. The method of claim 1, wherein the analyte comprises a drug, a metabolite, an inhibitor, a ligand, a receptor, a catalyst, a synthetic polymer, or an allosteric effector.

12. The method of claim 1, wherein the analyte is a biomolecule.

13. The method of claim 12, wherein the biomolecule comprises a nucleotide analyte, a peptidic analyte, or a saccharidic analyte.

14. The method of claim 1, wherein the necessary non-analyte original component comprises an original salt and the substitute component comprises a substitute salt.

15. The method of claim 14, wherein the original salt and the substitute salt function as buffer salts for the fluid sample, such that volatilization of the fluid sample results in gas phase extraction of the substitute buffer salt.

16. The method of claim 15, wherein the substitute salt comprises singly charged ions formed from weak acids or weak bases.

17. The method of claim 16, wherein the substitute salt comprises ammonium bicarbonate, ammonium formate, ammonium acetate, pyridinium acetate, pyridinium formate, ethylmorpholinium acetate, trimethylamino acetate, or trimethylamino formate.

18. The method of claim 17, wherein the substitute salt comprises ammonium bicarbonate, ammonium formate, or ammonium acetate.

19. The method of claim 1, wherein the substitute component is more volatile than both the necessary original component and/or the analyte.

20. The method of claim 1, wherein the reaction occurs during volatilization to provide for gas phase extraction of at least one non-analyte component in the fluid sample.

21. The method of claim 1, wherein the substitute component comprises a zwitterionic compound.

22. The method of claim 21, wherein the zwitterionic compound functions as a buffer salt for the fluid sample.

23. The method of claim 1, where the reaction involves chemical cleavage of a linkage in the substitute component.

24. The method of claim 23, wherein a reagent effective to chemically cleave the linkage is added to the fluid sample prior to volatilization.

25. The method of claim 1, wherein the reaction involves photolytic cleavage of a linkage in the substitute component.

26. The method of claim 25, wherein the fluid sample is irradiated during volatilization.

27. The method of claim 1, wherein the decomposition reaction involves thermal cleavage of a heat-labile linkage in the substitute component.

28. The method of claim 1, where the increase in analyte signal intensity and/or signal-to-noise ratio is at least 10%.

29. The improved method of claim 28, where the increase in analyte signal intensity and/or signal-to-noise ratio is at least 25%.

30. An improved method for determining the concentration of an analyte in a fluid sample that additionally comprises a necessary non-analyte original component, the method comprising volatilizing and ionizing the fluid sample, and introducing the ionized, volatilized sample into an ionic analyte detection device that provides an analyte signal proportional in intensity to the quantity of ionized analyte detected,
wherein the improvement comprises:
substituting for the necessary non-analyte original component a partially unsaturated, pre-aromatic zwitterionic compound that undergoes a reaction during volatilization of the fluid sample to yield an aromatic reaction product that functions as the original component in the fluid sample, is more volatile than the original component, the analyte, or both, and results in an increase in the intensity of the analyte signal and/or an increase in signal-to-noise ratio relative to the intensity of the analyte signal and signal-to-noise ratio obtained using the original component.

31. The method of claim 30, wherein the necessary non-analyte original component and the zwitterionic compound are buffer salts.

32. An improved method for determining the concentration of an analyte in a fluid sample that additionally comprises a necessary non-analyte original component, the method comprising volatilizing and ionizing the fluid sample, and introducing the ionized, volatilized sample into an ionic analyte detection device that provides an analyte signal proportional in intensity to the quantity of ionized analyte detected,
wherein the improvement comprises:
substituting for the necessary non-analyte original component a partially unsaturated, pre-aromatic zwitterionic compound that undergoes a decomposition reaction during volatilization of the fluid sample to yield a volatile aromatic compound, generate carbon dioxide, and release a nitrogen-containing compound.

33. The method of claim 32, wherein the nitrogen-containing compound comprises ammonia, a substituted or unsubstituted amine, or nitrogen gas.

34. A system for determining the concentration of an analyte in a fluid sample using a mass spectrometer, wherein the system comprises the fluid sample, an acoustic ejector to generate droplets of the fluid sample, and a means for volatilizing and ionizing the droplets prior to introduction into the mass spectrometer, wherein the fluid sample comprises, in addition to the analyte, a necessary non-analyte component that, upon volatilization of the fluid sample, undergoes a decomposition reaction to yield at least one aromatic reaction product that is more volatile than the analyte.

35. The system of claim 34, wherein the the necessary non-analyte component is a buffer salt, and volatilization of the fluid sample results in gas phase extraction of the buffer salt.

36. The system of claim 34, wherein the necessary non-analyte component contains a linkage that can be chemically, thermally, or photolytically cleaved to provide lower molecular weight reaction products.

37. The system of claim 36, wherein the necessary non-analyte component contains a linkage that can be photolytically cleaved, and the system further includes a source of radiation effective to cleave the linkage.

38. The system of claim 37, wherein the source of radiation is a source of ultraviolet light.

39. The system of claim 34, wherein the necessary non-analyte component comprises a partially unsaturated, pre-aromatic zwitterionic compound.

* * * * *